(12) United States Patent
Larsen

(10) Patent No.: US 11,304,427 B2
(45) Date of Patent: Apr. 19, 2022

(54) PROCESS FOR THE PRODUCTION OF A BACTERIALLY ENRICHED ANIMAL FEED COMPOSITION

(71) Applicant: Ebbe Busch Larsen, Odense (DK)

(72) Inventor: Ebbe Busch Larsen, Odense (DK)

(*) Notice: Subject to any disclaimer, the term of this patent is extended or adjusted under 35 U.S.C. 154(b) by 279 days.

(21) Appl. No.: 16/072,900

(22) PCT Filed: Jan. 25, 2017

(86) PCT No.: PCT/EP2017/051457
§ 371 (c)(1),
(2) Date: Nov. 5, 2018

(87) PCT Pub. No.: WO2017/129576
PCT Pub. Date: Aug. 3, 2017

(65) Prior Publication Data
US 2019/0082717 A1    Mar. 21, 2019

(30) Foreign Application Priority Data

Jan. 27, 2016    (DK) .......................... PA 2016 00051

(51) Int. Cl.
*A23K 10/18*    (2016.01)
*A23K 50/10*    (2016.01)
(Continued)

(52) U.S. Cl.
CPC .............. *A23K 10/18* (2016.05); *A23K 10/16* (2016.05); *A23K 50/10* (2016.05); *C12N 1/20* (2013.01)

(58) Field of Classification Search
None
See application file for complete search history.

(56) References Cited

U.S. PATENT DOCUMENTS

| 4,859,485 A * | 8/1989 | Linton .................. A23K 10/37 |
| | | 426/623 |
| 2002/0114866 A1 * | 8/2002 | Kartchner .............. A23K 30/20 |
| | | 426/55 |

(Continued)

FOREIGN PATENT DOCUMENTS

| EP | 2 573 165 A1 | 3/2013 |
| WO | 03/016460 A1 | 2/2003 |
| WO | 2007/072848 A1 | 6/2007 |

OTHER PUBLICATIONS

Machine translation from Google of WO2007/072848, dated Jun. 2007 (Year: 2007).*

(Continued)

*Primary Examiner* — Jenna A Watts
(74) *Attorney, Agent, or Firm* — Ware, Fressola, Maguire & Barber LLP

(57) ABSTRACT

The present invention relates to a process for the production of a bacterially enriched animal feed composition. The process comprises the steps of a) providing a proteinaceous feed material to be fermented; b) providing an inoculum comprising bacteria, and wherein the concentration of bacteria in the inoculum of step b) is sufficient to outgrow any bacteria, yeast or moulds present in the proteinaceous feed material of step a); c) combining the materials of steps a) and b) and fermenting the proteinaceous feed material of step a) using the inoculums of step b), thereby providing a fermented proteinaceous feed material; and d) adding methanotrophic bacteria to the fermented proteinaceous feed material to provide a bacterially enriched animal feed composition.

13 Claims, 5 Drawing Sheets

(51) Int. Cl.
*A23K 10/16* (2016.01)
*C12N 1/20* (2006.01)

(56) References Cited

U.S. PATENT DOCUMENTS

| | | |
|---|---|---|
| 2014/0037786 A1 | 2/2014 | Legarth |
| 2014/0112889 A1 | 4/2014 | Berger et al. |
| 2014/0154754 A1* | 6/2014 | Stephens ............... C12P 7/6409 435/128 |
| 2015/0344839 A1 | 12/2015 | Brooks et al. |

OTHER PUBLICATIONS

J. Jeyanathan et al., "The use of direct-fed microbials for mitigation of ruminant methane emissions: a review," Animal (2014), Nov. 25, 2013, pp. 250-261, vol. 8, No. 02, The Animal Consortium 2013, Cambridge University Press, XP055274392, GB, 12 pages.
Machine translation WO2007072848 A1 by ThomsonReuters, 18 pages, (Jun. 28, 2007).

* cited by examiner

PROCESS FOR THE PRODUCTION OF A BACTERIALLY ENRICHED ANIMAL FEED COMPOSITION

TECHNICAL FIELD OF THE INVENTION

The present invention relates to a process for the production of animal feed composition, and to the use of the produced feed composition for reducing the amount of methane emanating from the digestive tract of ruminants.

BACKGROUND OF THE INVENTION

Domestic livestock, such as cattle, buffalo, sheep, goats, and camels produce large amounts of methane as part of their normal digestive process. In addition, methane is produced when animals' manure is stored or managed in lagoons or holding tanks.

Methane is the second most prevalent greenhouse gas emitted. Methane's lifetime in the atmosphere is much shorter than carbon dioxide, but methane is more efficient at trapping radiation than carbon dioxide. Pound for pound, the comparative impact of methane on climate change is more than 25 times greater than carbon dioxide over a 100-year period.

Thus, there exists a need for a method for reducing the methane emission from livestock.

SUMMARY OF THE INVENTION

A first aspect relates to a process for the production of a bacterially enriched animal feed composition comprising the steps of:
a) providing a proteinaceous feed material to be fermented;
b) providing an inoculum comprising bacteria, and wherein the concentration of bacteria in the inoculum of step b) is sufficient to outgrow any bacteria, yeast or moulds present in the proteinaceous feed material of step a);
c) combining the materials of steps a) and b) and fermenting the proteinaceous feed material of step a) using the inoculums of step b), thereby providing a fermented proteinaceous feed material; and
d) adding methanotrophic bacteria to the fermented proteinaceous feed material to provide a bacterially enriched animal feed composition.

A second aspect relates to a bacterially enriched animal feed composition obtainable/obtained by the process according to the present invention.

A third aspect relates to the use of a bacterially enriched animal feed composition obtainable/obtained by the method according to the present invention to reduce amount of methane emanating from the digestive tract of ruminants (or livestock).

DETAILED DESCRIPTION OF THE INVENTION

Figure 1:
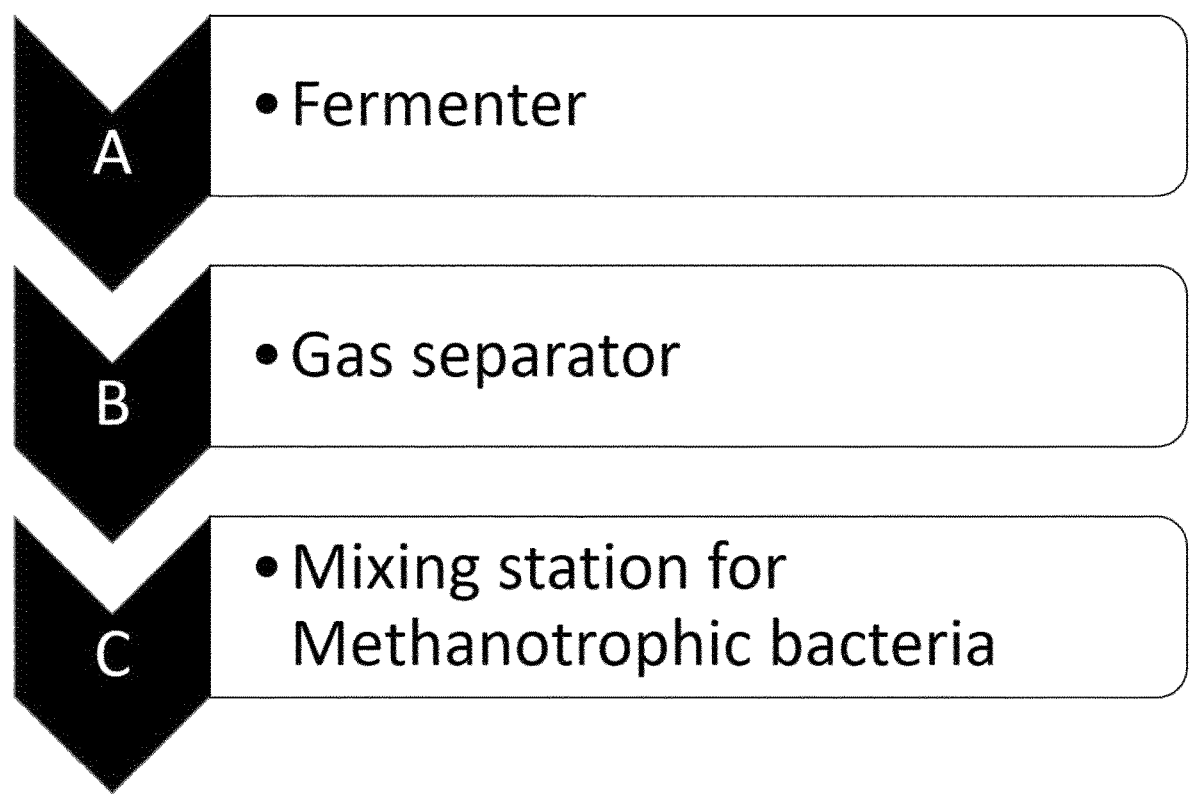
FIGS. 1-5 show different processes to produce a bacterially enriched animal feed in accordance with various embodiments of the invention.

A fermenter or bioreactor is defined here as a vessel suitable for conducting fermentation or for employing biocatalysts.

A fermentation process is defined as the growth or maintenance of living biocatalysts under aerobic, anaerobic or partially aerobic conditions such that a desired product is produced, whether that product is the cells themselves or substances produced by the cells or converted by the cells.

Living biocatalysts encompass microbial cells, animal cells, insect cells, plant cells, viruses, phage, prions, amoebae, algae, fungi, bacterial, prokaryotic or eukaryotic cells.

Non-living biocatalysts are dead cells or extracts from living or dead cells, e.g. enzymes.

The use of biocatalysts such as microbial cells or enzymes to make products is well known and has been practiced for centuries in what has become known as biotechnology processing. Typically, in biotech processes, microorganisms are cultivated in a tank (also called a fermentation tank, or simply a fermenter) into which the substrates necessary for the microorganisms to make the product are added.

Such cultivation processes typically occur in aqueous solutions (also called fermentation liquids, fermentation broths, or simply broths) containing a variety of substrates, such as carbon sources as well as nitrogen sources, phosphates, sulphates, as well as a wide variety of other components depending on the microorganism used and the products to be made. In many cases, the generic name fermentation is used for such processes, which may be carried out in the presence or the absence of oxygen or air.

In many cultivations, the microorganisms used require oxygen, and this must be added. Pure gaseous oxygen or oxygen-enriched air may also be used as an oxygen source. Cultivations, in which oxygen is added are called aerobic fermentations or aerobic cultivations. In some cases, other substrates used by the microorganisms are added as gases to the solution, and may for example be carbon sources such as methane. Waste products are also formed during fermentation. One waste product that is normally produced in the largest amount is carbon dioxide. The addition of gaseous substrates such as oxygen or methane to fermentation liquid is problematic, since the microorganisms cannot use the gases directly. The gases must therefore be dissolved in the fermentation broth, after which they are taken up by the microorganisms and used as an energy source and/or for microbial growth.

The transfer rate of substances from the gas phase into the liquid phase can be improved if very small bubbles are used, or if a higher pressure (i.e. the pressure in the headspace of the fermenter is above atmospheric pressure) is used in the fermenter, or if the temperature of the broth is reduced. Since microorganisms are sensitive living cells, significant reduction of the temperature is not possible without affecting the growth rate of the microorganisms.

A large amount of energy is typically used in conventional fermentation tanks to ensure that sufficient amounts of the gaseous substrates are dissolved in the fermentation broth.

Conventional fermenters are tall stirred tanks in which the mixing of gases with the fermentation liquid is effected by means of stirrer blades placed centrally in the fermenter. The stirrer blades generate turbulence in the liquid, which means that gas, usually injected at the bottom of the reactor, will be dissipated in the liquid in the form of small fine gas bubbles.

Other fermenter types have also been designed with the intention of reducing energy consumption for mixing but still ensuring sufficient mass transfer of gases to the liquid phase. These fermenters are often called air lift fermenters, jet loop fermenters or U-loop fermenters.

Different types of airlift reactors have been designed in order to avoid the mechanical stirring. The majority of these reactors are so-called loop reactors having two sections: an up-flow part and a down-flow part, which are interconnected at both ends. Gases are supplied as small bubbles at the bottom of the reactor in the up-flow part usually in a nozzle arrangement. The bubbles mix with the liquid, whereby the total density is reduced and the gas-liquid mixture ascends while being displaced by new liquid emerging from the down-flow part. The gas-liquid mixture moves up through the up-flow part of the reactor and releases gas bubbles at the top. Then, the liquid descends down through the down-flow part. In order to obtain a long residence time for the gas bubbles in the liquid. Airlift reactors are conventionally very tall slender reactors, and the gas must be supplied at a high, but variable, pressure for overcoming the hydrostatic pressure at the bottom of the reactor.

The type of fermenter is, as such, not relevant for the present invention.

A first aspect relates to a process for the production of a bacterially enriched animal feed composition comprising the steps of:

a) providing a proteinaceous feed material to be fermented;
b) providing an inoculum comprising bacteria, and wherein the concentration of bacteria in the inoculum of step b) is sufficient to outgrow any bacteria, yeast or moulds present in the proteinaceous feed material of step a);
c) combining the materials of steps a) and b) and fermenting the proteinaceous feed material of step a) using the inoculums of step b), thereby providing a fermented proteinaceous feed material; and
d) adding methanotrophic bacteria to the fermented proteinaceous feed material to provide a bacterially enriched animal feed composition.

The term "Inoculation" refers to the placement of microorganisms (e.g. lactic acid producing bacteria) that will grow when implanted in a culture medium, such as a fermentation tank comprising media to be fermented. "Inoculum" refers to the material used in an inoculation, for example a composition comprising microorganisms, which is employed to prime a process of interest. For example, an inoculum where the bacteria are essentially lactic acid producing bacteria may be used to direct a lactic acid formation process in a culture medium in a fermentation tank comprising said media (e.g. a feed product). Thus, "to inoculate" refers to the transfer of the inoculum to the media to be processed, for example, the transfer of the inoculums to a proteinaceous feed material to be fermented. The primary inoculum refers to the generation of the initial inoculum in a series of repeated similar of essentially identical inoculation process, for example one or more repetitions of a fermentation process. An aliquot of the product of the formation process may be used to inoculate a new process of fermentation. Thus, the inoculation may be a fermented feed product, which comprises viable lactic acid producing bacteria in sufficient amount to prime a lactic acid fermentation process of another proteinaceous feed material to be fermented. The inoculum may be a in a liquid form, dry form, or essentially dry form. The moisture % of the inoculum may be adjusted in order to optimize the fermentation process. Thus, the inoculum used in the processes of the present invention may be a fermented feed product.

In one or more embodiments, the inoculum is provided as essentially pure viable bacteria (such as bacteria in freeze dried form) or bacteria suspended in a suitable media prior to the application (such as a water, buffer or a growth media).

The proportion of the inoculums added to the proteinaceous feed material may vary. In case it is considered that the load of undesirable microbes are significant in the proteinaceous feed material, the proportion of the inoculum in the fermentation mixture (inoculum+proteinaceous feed material+optionally additional water) may be increased to insure that the fermentation is directed by the microbes (e.g. lactic acid bacteria) of the inoculums. Thus, the inoculum may be provided with a concentration of bacteria in the inoculum sufficient to outgrow any bacteria, yeast or moulds present in the product of step a).

Accordingly, in one embodiment of the invention, the proportion of said inoculum in the combined materials provided in step c), is within the range of 0.1-99.9 vol-%, 1-99 vol-%, 5-95 vol-%, 10-90 vol-%, 15-85 vol-%, 20-80 vol-%, 25-75 vol-%, 30-70 vol-%, 35-65 vol-%, 40-60 vol-%, 45-55 vol-%, preferably around 1-5 vol-%, such as 2-4 vol-%.

In one or more embodiments, the bacteria in the inoculum are essentially lactic acid-producing bacteria, and where the fermentation process is performed under anaerobic conditions.

The lactic acid bacteria comprise a Glade of Gram positive, low-GC, acid tolerant, non-sporulating, non-respiring rod or cocci that are associated by their common metabolic and physiological characteristics. These bacteria, usually found in decomposing plants and lactic products produce lactic acid as the major metabolic end-product of carbohydrate fermentation. This trait has historically linked lactic acid bacteria with food fermentations as acidification inhibits the growth of spoilage agents. Proteinaceous bacteriocins are produced by several lactic acid bacteria strains and provide an additional hurdle for spoilage and pathogenic microorganisms. Furthermore, lactic acid and other metabolic products contribute to the organoleptic and textural profile of a food item. The industrial importance of the lactic acid bacteria is further evidenced by their generally regarded as safe (GRAS) status, due to their ubiquitous appearance in food and their contribution to the healthy microflora of human mucosal surfaces.

In the present invention, the lactic acid-producing bacteria in inoculom used for fermentation are mainly and non-exclusively lactic acid bacteria of the genus *Enterococcus, Lactobacillus, Pediococcus* or *Lactococcus*, or combinations thereof. In one embodiment of the present invention, the inoculum comprises at least one lactic acid bacterium species selected from the group consisting of one or more of *Enterococcus* spp., *Lactobacillus* spp., *Lactococcus* spp., and *Pediococcus* spp. In yet a further embodiment of the invention, the lactic acid bacteria are selected from the group consisting of one or more of *Enterococcus faecium, Lactobacillus rhamnosus, Lactobacillus plantarum, Pediococcus acidililactili,* and *Pediococcus pentosaceus*. In further embodiment, the lactic acid producing bacteria are of the order Lactobacillales. The lactic acid-producing bacteria can also be selected from *Lactobacillus* spp., *Pediococcus* spp., *Enterococcus* spp., and *Lactococcus* spp. or a combination thereof. In yet another embodiment, the lactic acid-producing bacteria comprise *Pediococcus pentosaceus, Pendiococcus acidilactici* and *Lactobacillus plantarum, Lactobacillus rhamnosus*, and *Enterococcus faecium*, or a combination thereof. In still another embodiment, the lactic acid bacteria comprise *Enterococcus faecium* and/or *Lactobacillus rhamnosus*. In a further embodiment, the lactic acid bacteria comprise one or more of *Enterococcus faecium* MCIMB 30122, *Lactobacillus rhamnosus* NCIMB 30121, *Pediococcus pentosaceus* HTS (LMG P-22549), *Pendiococcus acidilactici* NCIMB 30086 and/or *Lactobacillus plantarum* LSI (NCIMB 30083).

The fermentation process in step f) can be controlled by varying e.g. temperature and time to optimize the fermentation reaction. Thus, in yet an embodiment step f) is performed at a temperature within the range of 15-45° C., such as 15-40° C., such as 25-35° C., such as 30-40° C., such as 15-20° C., or such as 40-45° C.

In another embodiment, step c) is performed for a period within the range of 1-10 days, such as 2-9 days, such as 3-8 days, such as 4-7 days, such as 5-6 days, preferably at least 1 day, such as at least 2 days, such as at least 3 days. When the reaction runs for longer periods, the actual fermentation may decrease or cease completely due to lowered viability of the bacteria. However, in the case where enzymes are added, the enzymatic degradation may continue, and hence, it may be advantageous to continue the process. Furthermore, since the pH has been lowered during fermentation, contamination from undesired micro-organisms is minimized.

In one or more embodiments, the concentration of added methanotrophic bacteria in the bacterially enriched animal feed composition is sufficient to reduce amount of methane emanating from the digestive tract of ruminants (or livestock).

The methanotrophic bacteria may be added as a) an inoculum comprising essentially methanotrophic bacteria and/or b) an isolated methanotrophic bacteria or spore.

Accordingly, in one embodiment of the invention, the proportion of said added inoculum comprising essentially methanotrophic bacteria in the bacterially enriched animal feed composition is within the range of 0.1-99.9 vol-%, 1-99 vol-%, 5-95 vol-%, 10-90 vol-%, 15-85 vol-%, 20-80 vol-%, 25-75 vol-%, 30-70 vol-%, 35-65 vol-%, 40-60 vol-%, 45-55 vol-%, preferably around 1-5 vol-%, such as 2-4 vol-%. Thus, the inoculum is provided with a concentration of methanotrophic bacteria sufficient to reduce amount of methane emanating from the digestive tract of ruminants (or livestock).

In one or more embodiments, the methanotrophic bacteria are selected from the group consisting of *Methylomonas, Methylobacter, Methylococcus, Methylosinus*, and mixtures thereof.

In one or more embodiments, the methanotrophic bacteria are selected from the group consisting of *Methylococcus Capsulatus*.

In one or more embodiments, the fermented proteinaceous feed material is transferred to a flash tank prior to step d) to enable volatile material to evaporate.

In one or more embodiments, the fermented proteinaceous feed material is transferred to a separator, such as a centrifuge, adapted for removing at least a part of the liquid fraction of the fermented proteinaceous feed material, prior to step d).

In one or more embodiments, the fermented proteinaceous feed material is transferred to a sterilization unit prior to step d).

A second aspect relates to a bacterially enriched animal feed composition obtainable/obtained by the process according to the present invention.

A third aspect relates to the use of a bacterially enriched animal feed composition obtainable/obtained by the method according to the present invention to reduce amount of methane emanating from the digestive tract of ruminants (or livestock).

Figure 2:
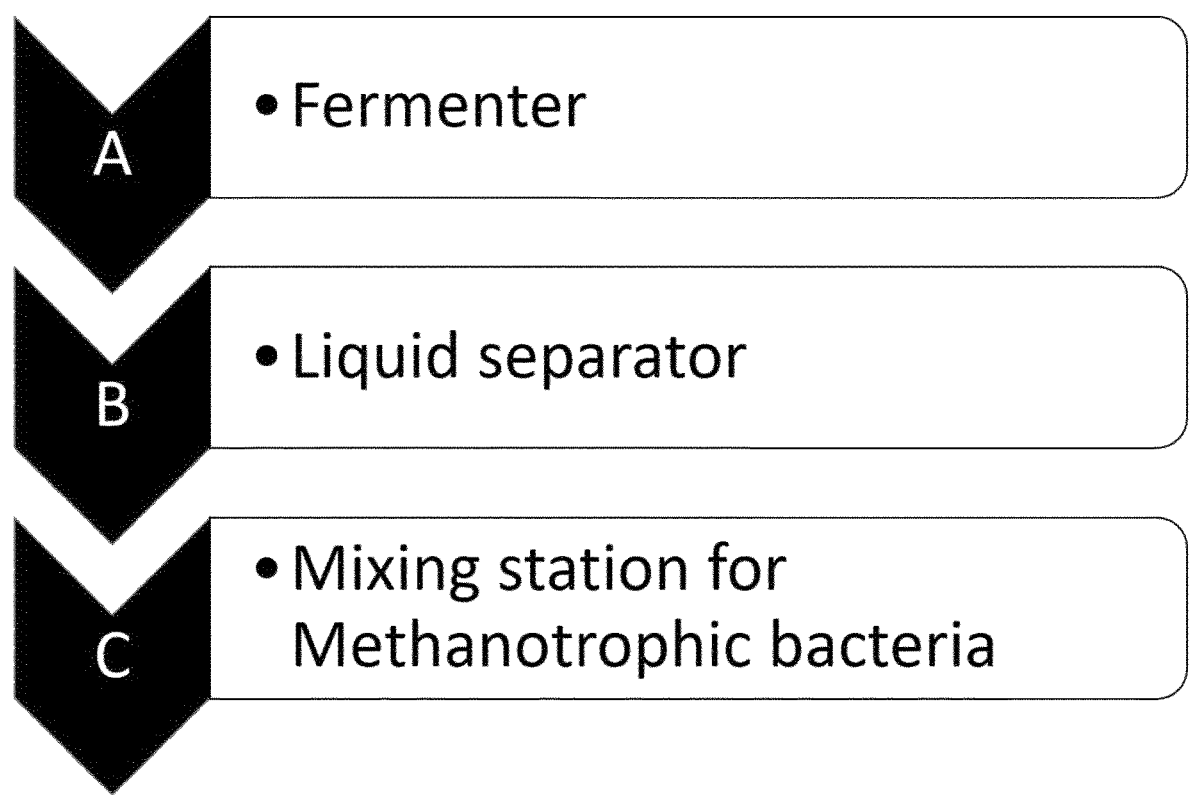
Figure 3:
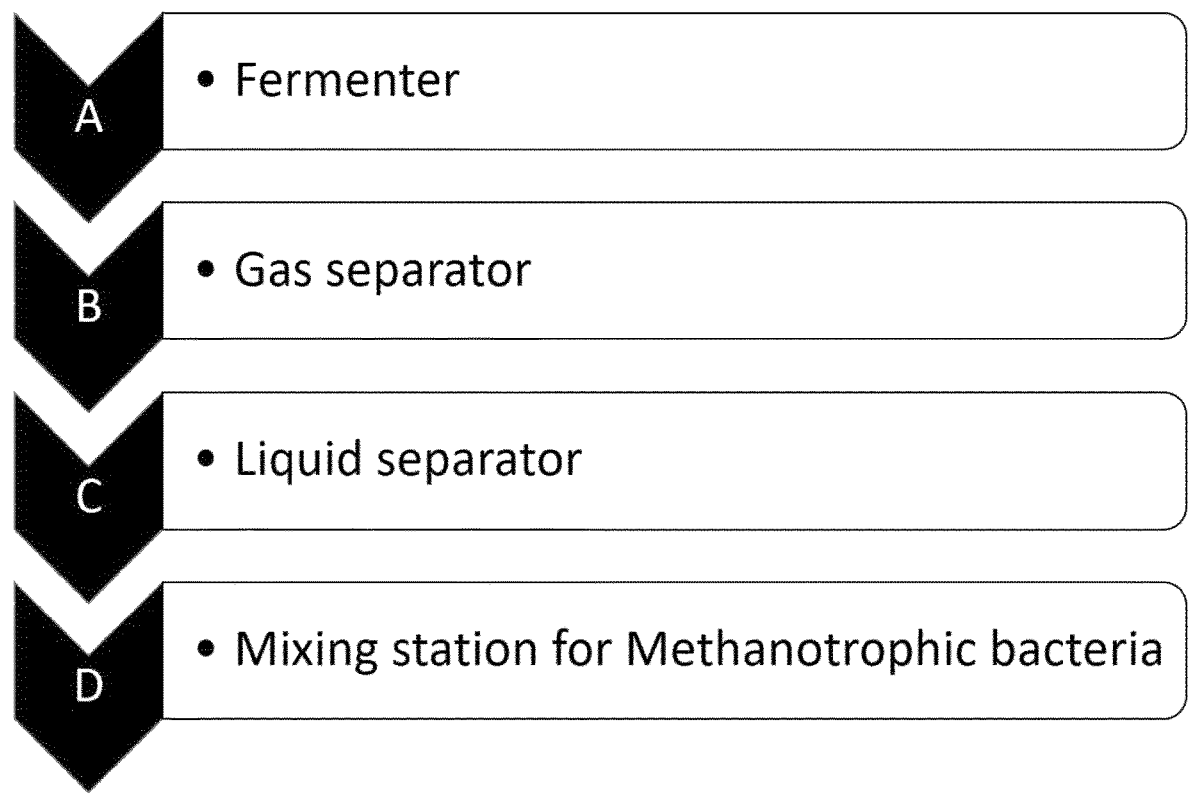
Figure 4:
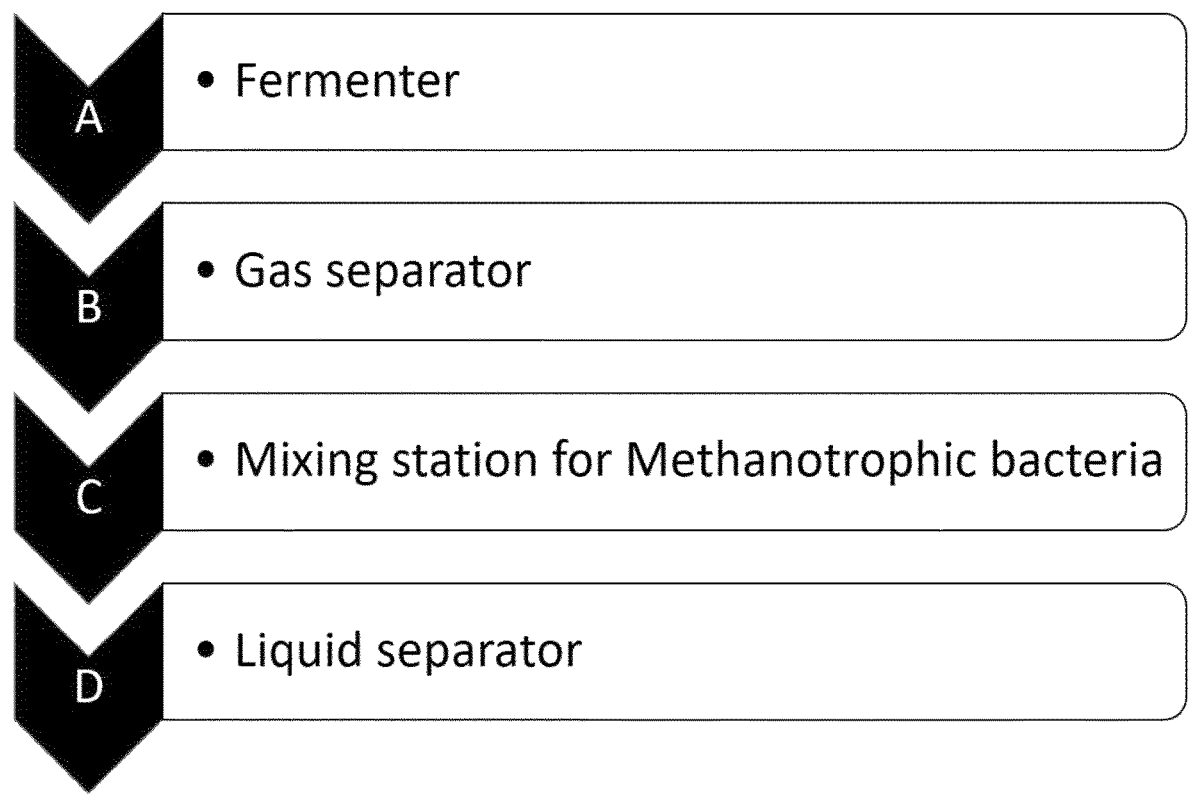
Figure 5:
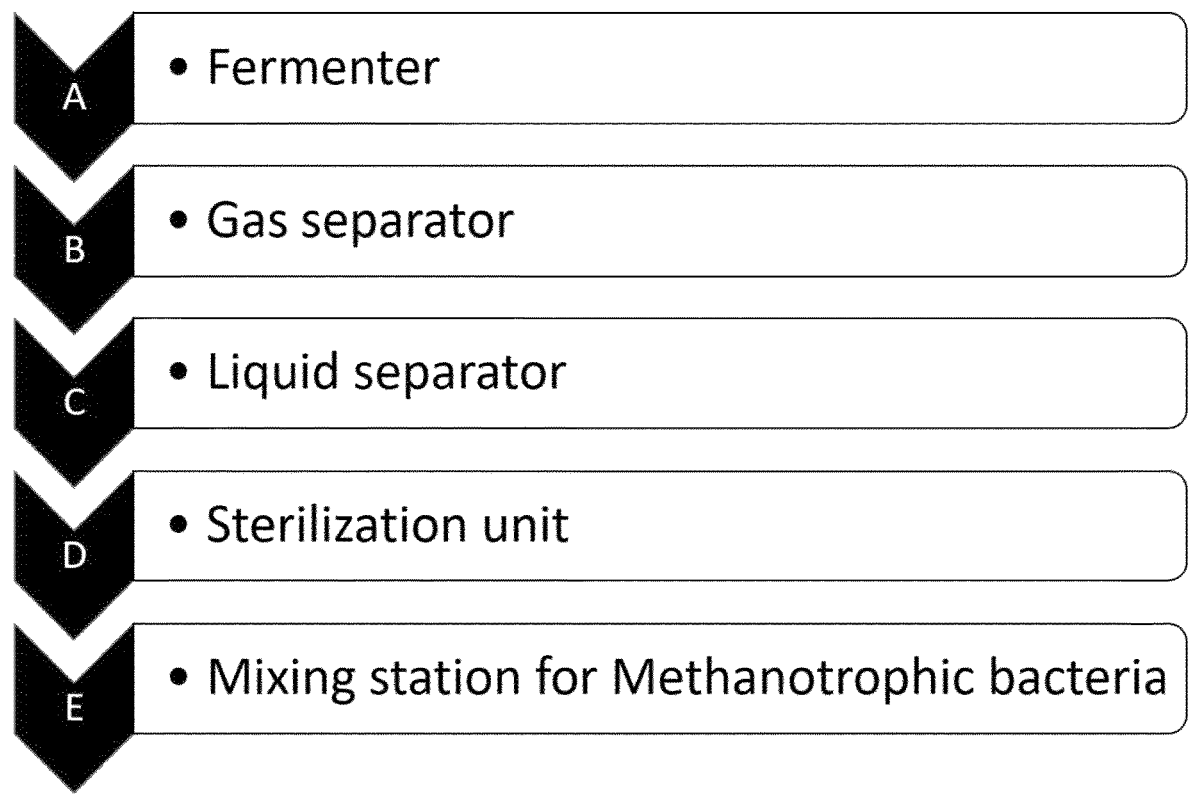

Byproducts from the fermentation process or initial components of the proteinaceous feed material may need to be removed before the bacterially enriched animal feed composition is suitable for use. In FIG. 1, a process is shown where the fermented proteinaceous feed material is transferred to a gas separator, such as a flash tank, prior to step d) to enable volatile material to evaporate. In FIG. 2, the fermented proteinaceous feed material is transferred to a liquid separator, such as a centrifuge, adapted for removing at least a part of the liquid fraction of the fermented proteinaceous feed material, prior to step d). In FIG. 3, the fermented proteinaceous feed material is first transferred to a gas separator, such as a flash tank, to enable volatile material to evaporate. Then the degassed fermented proteinaceous feed material is transferred to a liquid separator, such as a centrifuge, adapted for removing at least a part of the liquid fraction of the fermented proteinaceous feed material. Both steps are prior to step d). In FIG. 4, the fermented proteinaceous feed material is first transferred to a gas separator, such as a flash tank, to enable volatile material to evaporate. Then the degassed fermented proteinaceous feed material is transferred to a mixing station, where step d) is performed. The bacterially enriched animal feed composition is then transferred to a liquid separator, such as a centrifuge, adapted for removing at least a part of the liquid fraction of the bacterially enriched animal feed composition. In FIG. 5, the fermented proteinaceous feed material is first transferred to a gas separator, such as a flash tank, to enable volatile material to evaporate. Then the degassed fermented proteinaceous feed material is transferred to a liquid separator, such as a centrifuge, adapted for removing at least a part of the liquid fraction of the fermented proteinaceous feed material. Then the degassed and deliquefied fermented proteinaceous feed material is transferred to a sterilization unit. All steps are prior to step d).

The invention claimed is:

1. A process for the production of a bacterially enriched animal feed composition comprising the steps of:
   a) providing a proteinaceous feed material to be fermented;
   b) providing an inoculum comprising lactic acid producing bacteria, and wherein the concentration of bacteria in the inoculum of step b) is sufficient to outgrow any bacteria, yeast or moulds present in the proteinaceous feed material of step a);
   c) combining the materials of steps a) and b) and fermenting the proteinaceous feed material of step a) using the inoculums of step b), thereby providing a fermented proteinaceous feed material; and
   d) adding methanotrophic bacteria to the fermented proteinaceous feed material to provide a bacterially enriched animal feed composition, wherein the methanotrophic bacteria is added to within a range of 1-55 vol-%.

2. The process according to claim 1, wherein the concentration of added methanotrophic bacteria in the bacterially enriched animal feed composition is sufficient to reduce amount of methane emanating from the digestive tract of ruminants or livestock.

3. The process according to claim 1, wherein the bacteria in the inoculum consist essentially of lactic acid-producing bacteria, and where the fermentation process is performed under anaerobic conditions.

4. The process according to claim 1, wherein the methanotrophic bacteria are selected from the group consisting of *Methylomonas, Methylobacter, Methylococcus, Methylosinus*, and mixtures thereof.

5. The process according to claim 1, wherein the methanotrophic bacteria are selected from the group consisting of *Methylococcus Capsulatus*.

6. The process according to claim 1, wherein the fermented proteinaceous feed material is transferred to a gas separator prior to step d) to enable volatile material to evaporate.

7. The process according to claim 1, wherein the fermented proteinaceous feed material is transferred to a liquid separator, prior to step d).

8. The process according to claim 1, wherein the fermented proteinaceous feed material is transferred to a sterilization unit prior to step d).

9. The process according to claim 1, wherein the fermented process in step c) is performed at a temperature within the range of 15-45° C.

10. The process according to claim 1, wherein the fermented process in step c) is performed for a period within the range of 1-10 days.

11. The process according to claim 1, wherein the methanotrophic bacteria is added to the bacterially enriched animal feed composition within a range of 1-5 vol-%.

12. The process according to claim 6, wherein the gas separator is a flash tank.

13. The process according to claim 7, wherein the liquid separator is a centrifuge.

* * * * *